United States Patent [19]

Kramer et al.

[11] Patent Number: 4,688,570
[45] Date of Patent: Aug. 25, 1987

[54] OPHTHALMOLOGIC SURGICAL INSTRUMENT

[75] Inventors: Steven G. Kramer; Edward Q. Yavitz, both of San Francisco, Calif.

[73] Assignee: The Regents of the University of California, Berkeley, Calif.

[21] Appl. No.: 483,510

[22] Filed: May 9, 1983

Related U.S. Application Data

[63] Continuation of Ser. No. 241,827, Mar. 9, 1981, abandoned.

[51] Int. Cl.⁴ ............................................. A61B 17/32
[52] U.S. Cl. ................................. 128/305; 128/303 R
[58] Field of Search ............... 128/305, 305.1, 303 R; 30/303, 114

[56] References Cited

U.S. PATENT DOCUMENTS

| | | | |
|---|---|---|---|
| 2,480,737 | 8/1949 | Jayle | 128/305 |
| 2,932,296 | 4/1960 | Sanders | 128/305 |
| 3,074,407 | 1/1963 | Moon et al. | 128/303 R |
| 3,902,475 | 9/1975 | Begg et al. | 128/2 R |
| 4,180,075 | 12/1979 | Marinoff | 128/305 |
| 4,205,682 | 6/1980 | Crock et al. | 128/305 |
| 4,406,285 | 9/1983 | Villasenor et al. | 128/305 |
| 4,526,171 | 7/1985 | Schachar | 128/305 |
| 4,619,259 | 10/1986 | Graybill et al. | 128/305 |

OTHER PUBLICATIONS

"Radial Keratotomy", by Schachar et al, pp. 201–212 (1980).
Martin Motor Trephine Pamphlet (5/1977).

Primary Examiner—Michael H. Thaler
Attorney, Agent, or Firm—Phillips, Moore, Lempio & Finley

[57] ABSTRACT

A surgical instrument in the form of a template comprises at least one slit formed therethrough to guide either pivotal or dragging cutting movement of a surgical blade of a scalpel therein. The instrument is preferably fixedly held, by suction, over a body area to be incised. In one embodiment, the scalpel is pivotally mounted adjacent to the slit for arcuate movement about a fixed pivot to ensure accurate and reproducible incisions. In a second embodiment, grooves are formed alongside the slit to guide dragging movement of the blade. The instrument is particularly adapted for radial keratotomy wherein a plurality of radially extending and circumferentially spaced slits are formed through the instrument. The surgical blade can be adapted for adjustment, on an angularly offset handle secured thereto, to selectively vary the depth of the incision.

31 Claims, 15 Drawing Figures

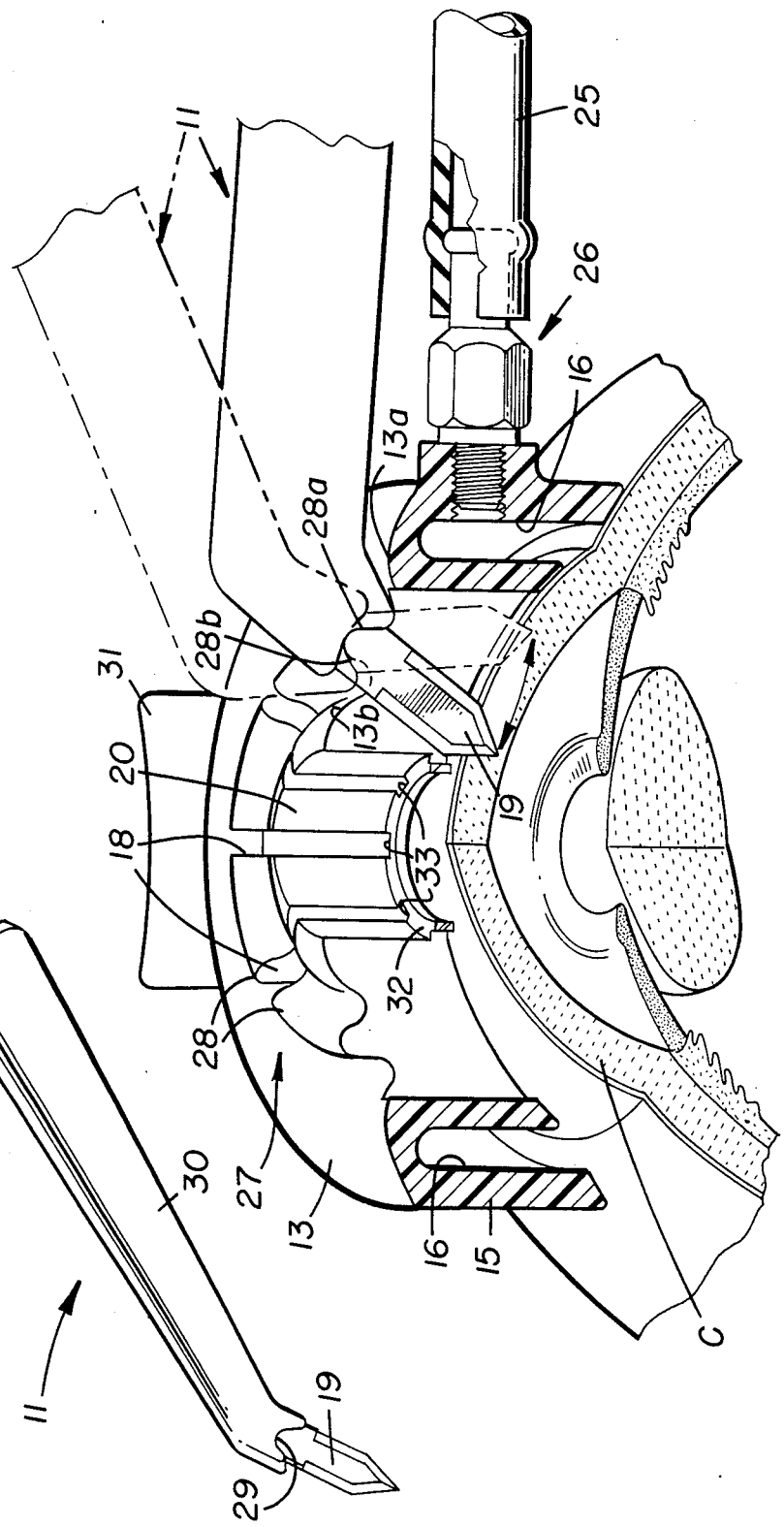

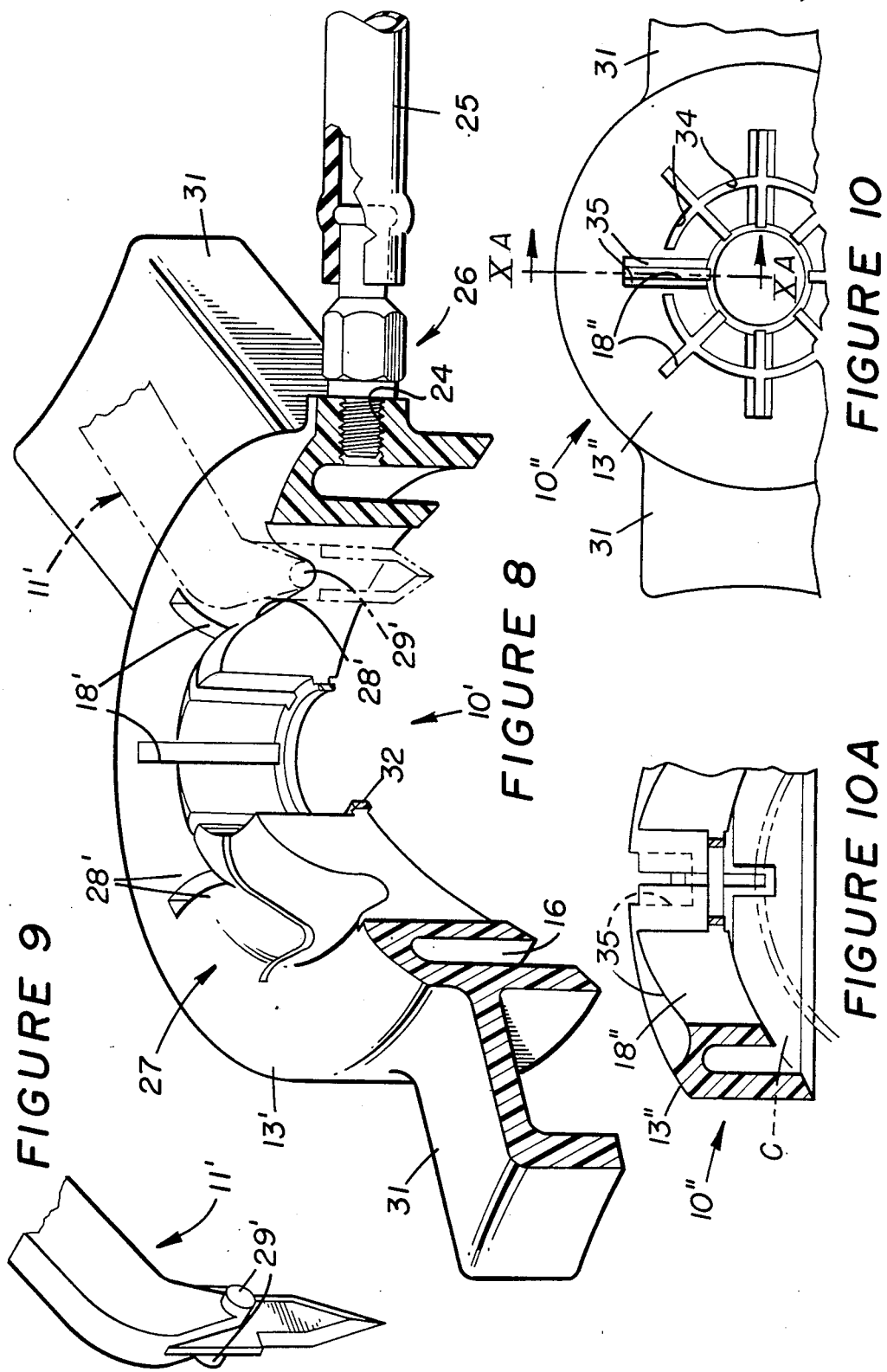

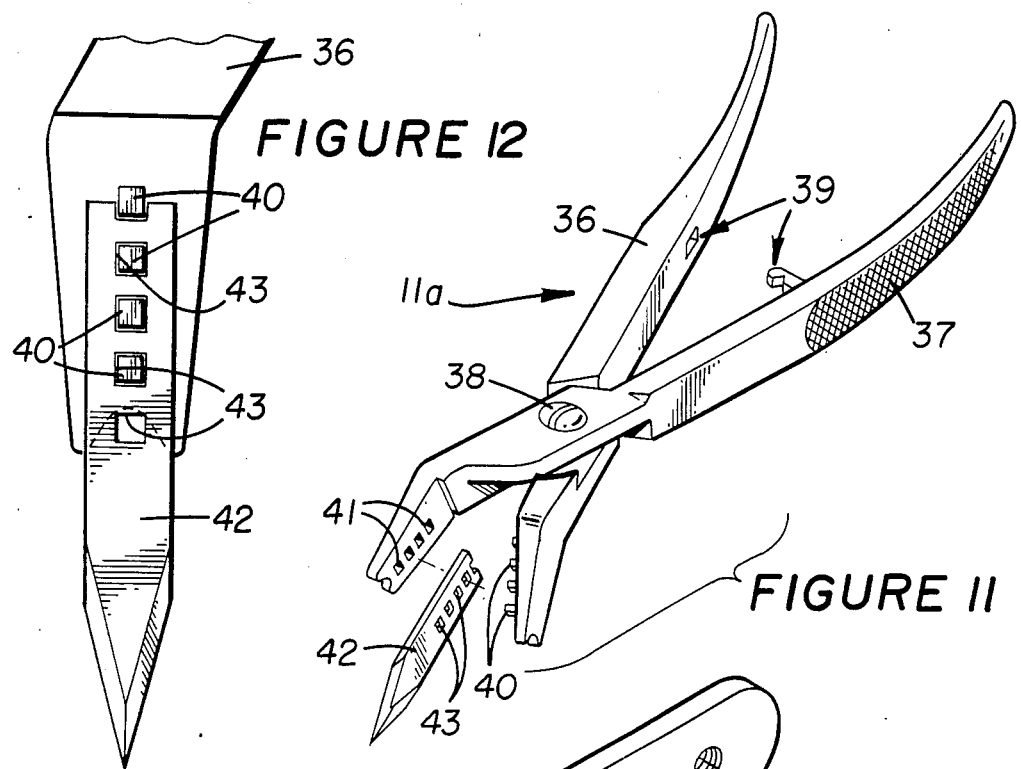
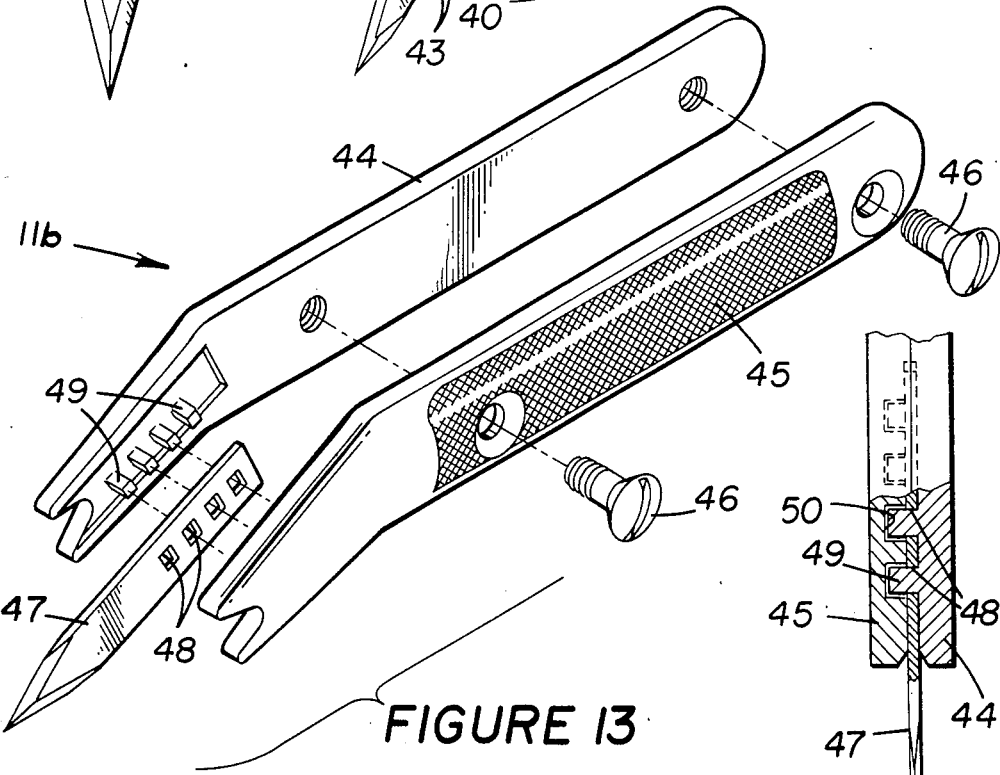

4,688,570

OPHTHALMOLOGIC SURGICAL INSTRUMENT

This is a continuation of Ser. No. 241,827, filed Mar. 9, 1981, now abandoned.

TECHNICAL FIELD

This invention relates generally to a surgical instrument and more particularly to a surgical instrument particularly adapted for radial keratotomy and the like.

BACKGROUND ART

The advent of radial keratotomy for correcting mild to moderate myopia (near-sightedness) has given rise to the need for a surgical instrument for effecting the operation in a well-controlled and reproducible manner. The operation essentially consists of making corneal incisions of desired depth and length for the purpose of changing intra-stromal corneal relationships in order to permanently flatten the cornea and reduce myopia and astigmatism. Currently, the incisions are made individually and consecutively by hand.

For example, the so-called Fyodorov method includes the marking of the center of the cornea and the desired incision lines with a wheel-spoke type solid template. The template is pressed onto the cornea to make an impression of the wheel-spoke configuration thereon, whereafter the surgeon will slice along each line with a surgical blade. The surgeon must oftentimes repeat the blade stroke and will occasionally and inadvertently perforate the cornea.

This conventional freehand method has a tendency to effect unequal and non-radial incisions. In addition, each new incision will decrease corneal rigidity so that subsequent incisions will tend to be made deeper and not as straight as the prior ones. Another problem encountered with the above freehand method is one of the surgeon knowing when to begin and end a particular incision. If the incision should transverse the limbus, for example, undue bleeding and poor healing could result. Also, incisions of unequal length could create, rather than cure, astigmatism. Furthermore, such a freehand method is not conducive to making an incision across or subsequent to a previously-made incision since the latter incision will tend to gape.

The present invention is directed to overcoming one or more of the problems as set forth above.

DISCLOSURE OF INVENTION

The present invention is directed to a cup-shaped surgical instrument, particularly adapted for radial keratotomy, comprising an upper wall, radially spaced inner and outer walls defining a generally annular suction chamber and a plurality of circumferentially disposed struts secured to the inner wall and extending radially outwardly into the suction chamber. A slit is formed axially through each of the struts to accommodate and guide a surgical incision forming means and access means is formed through the instrument for drawing a vacuum in the suction chamber.

BRIEF DESCRIPTION OF THE DRAWINGS

Other objects and advantages of this invention will become apparent from the following description and accompanying drawings wherein;

FIG. 6 is an enlarged sectional view, similar to FIG. 2, illustrating disposition of the instrument over the eye of a patient during the radial keratotomy operation and the cutting action of a scalpel pivotally associated therewith;

FIG. 7 is an isometric view illustrating the scalpel;

FIG. 8 is a sectional view, similar to FIG. 6, illustrating a modified instrument and scalpel associated therewith;

FIG. 9 is a partial isometric view of the latter scalpel;

FIG. 10 is a partial top plan view of a further modified instrument;

FIG. 10A is a sectional view, taken in the direction of arrows XA—XA in FIG. 10; and FIGS. 11–14 illustrate two additional scalpel embodiments, each having an adjustable blade.

BEST MODE OF CARRYING OUT THE INVENTION

Figures 1, 2:
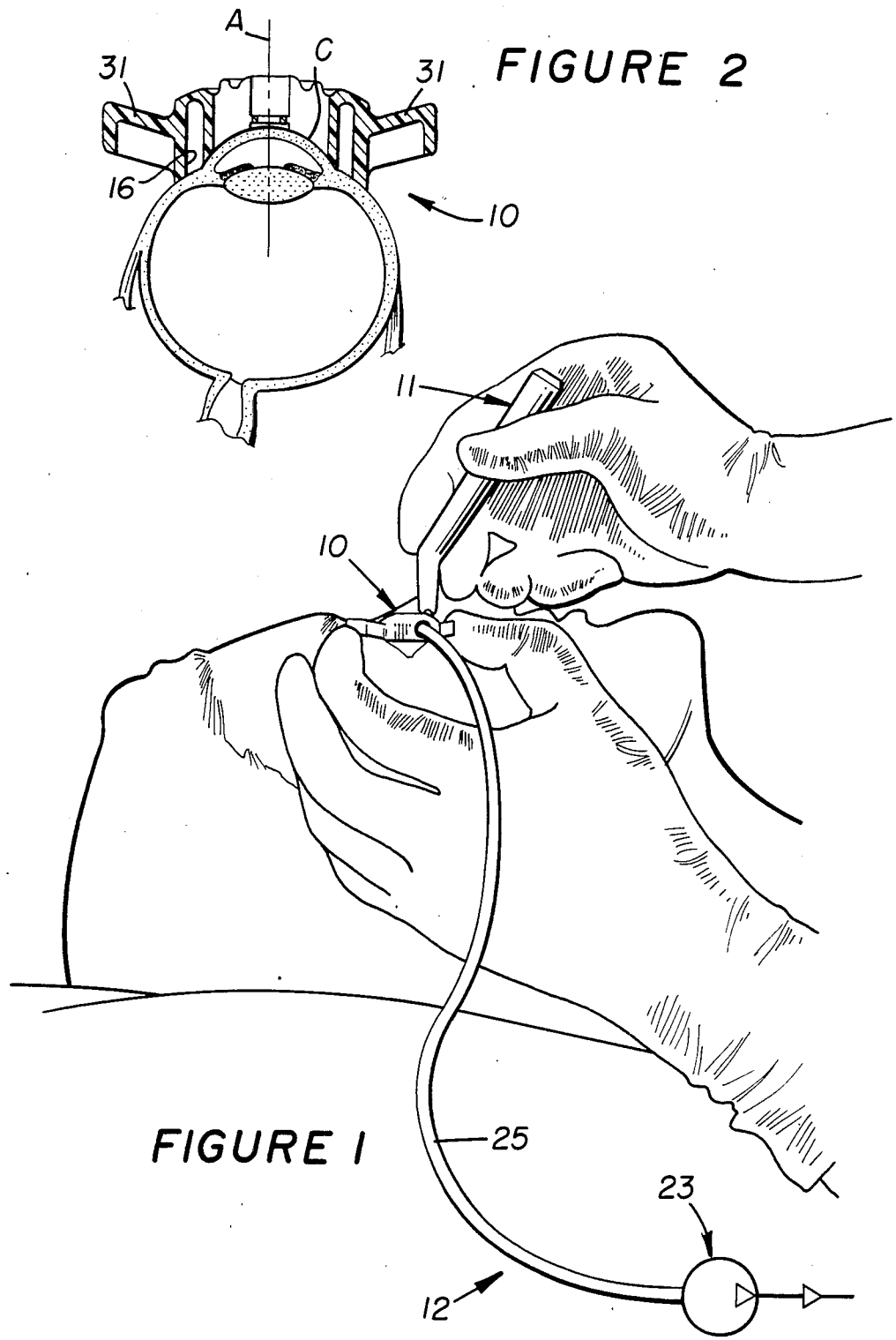
FIG. 1 illustrates a surgeon performing radial keratotomy on a patient with use of a surgical instrument embodying this invention.
FIG. 2 is an enlarged sectional view illustrating the disposition of the instrument on an eye of the patient during the radial keratotomy operation.

FIG. 1 illustrates a surgical instrument 10 positioned on an eye of a patient during a radial keratotomy operation. Although the instrument has particular application as an opthalmologic surgical instrument, it will be hereinafter understood by those skilled in the surgical arts that the instrument will find other applications wherein incisions must be precisely made in a reproducible manner on a patient. The instrument is in the form of a template adapted to pivotally mount an incision forming means, shown in the form of a scalpel 11 thereon so that the depth and length of the incision can be closely controlled and reproduced with accuracy. As described more fully hereinafter, a means 12 is provided for drawing an at least partial vacuum within instrument 10 to releasably secure the instrument in place over the eye of the patient by suction, as shown in FIGS. 2 and 6.

Figure 3:
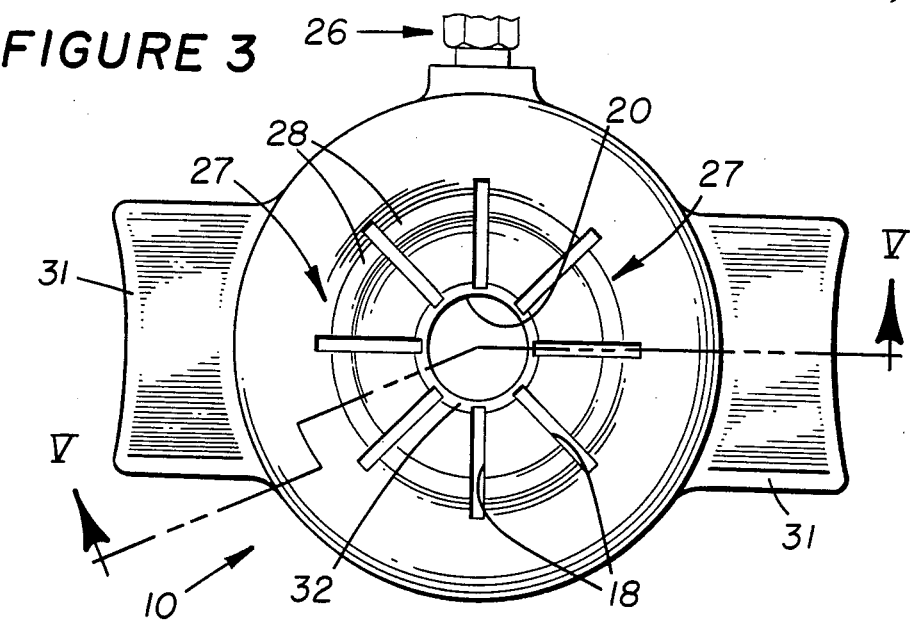
FIG. 3 is an enlarged, top plan view of the instrument.
Figure 5:
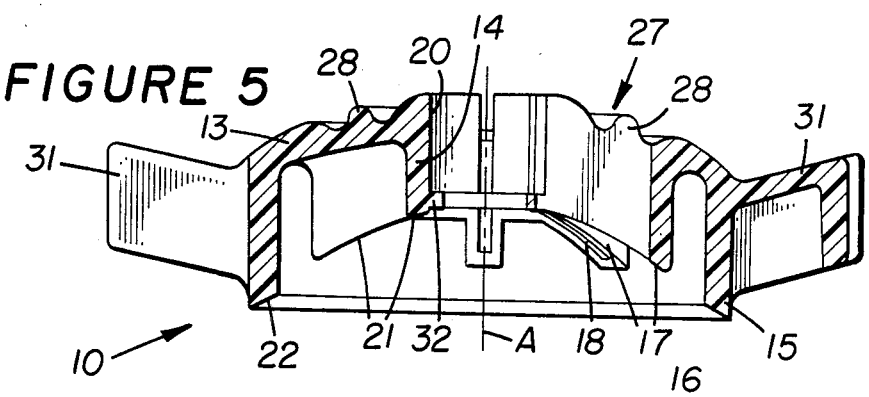
FIG. 5 is a sectional view of the instrument, taken in the direction of arrows V—V in FIG. 3.
Figure 4:
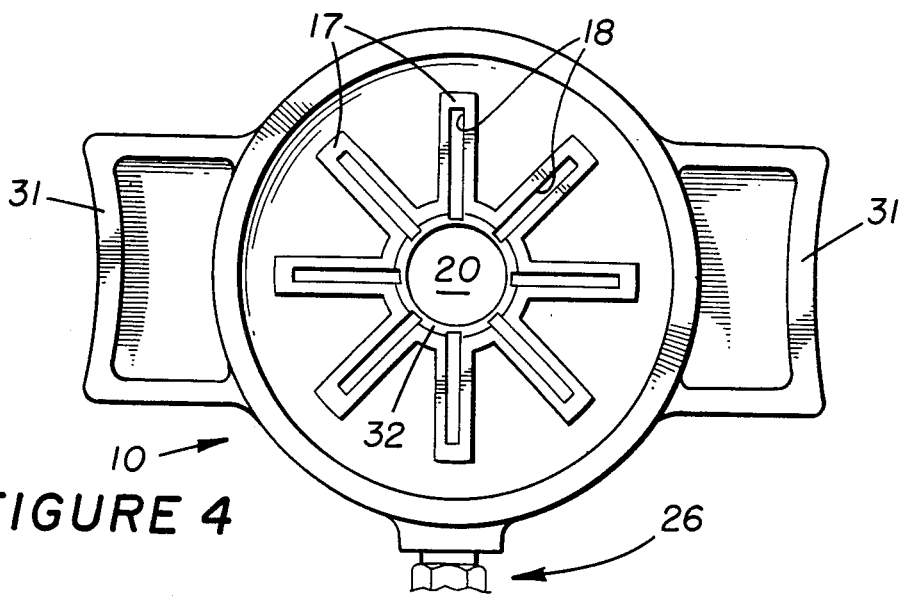
FIG. 4 is an enlarged, bottom plan view of the instrument.

Referring to FIGS. 3–5, instrument or template 10 is cup-shaped to have an upper wall 13 and inner and outer walls 14 and 15, respectively, spaced radially from each other to define a generally annular suction chamber 16 therebetween, which is open only at a lower end thereof. Inner wall 14 is interrupted by a plurality of circumferentially spaced spoke-like struts 17 formed integrally therewith to extend radially outwardly from a longitudinal or central axis A of the instrument and into chamber 16. A slit 18 is formed axially through each strut 17 and extends radially outwardly from axis A to accomodate a surgical blade 19 of scalpel 11 therein (FIG. 7).

Instrument 10 is preferably composed of a transparent plastic material to enable the surgeon to observe the operation directly. The instrument can be formed by conventional molding methods, such as injection molding. A circular aperture 20, interrupted by slits 18, is formed through upper wall 13 and struts 17 of the instrument to aid in properly positioning central axis A of the instrument in alignment with the visual and central axis of a cornea C, as shown in FIG. 2. Lower surfaces 21 on the bases of inner wall 14 and ribs 17 are formed generally semi-spherically or otherwise arcuately to closely match the curved shape of the cornea, which can change from patient to patient. In addition, lower surfaces 22 on the base of outer wall 15 are also shaped in this manner and extend axially beyond surfaces 21 to closely match the curvature of the eye, radially outwardly from the cornea.

When instrument 10 is positioned on an eye, as shown in FIGS. 1, 2, and 6, surfaces 21 and 22 will provide static seals thereat whereby an at least partial vacuum can be drawn in isolated and sealed chamber 16. Means 12 for drawing a vacuum in sealed suction chamber 16 may comprise a standard vacuum pump 23 suitably connected to an access or opening 24, formed through outer wall 15, to communicate with chamber 16 via a flexible tube 25 and a fitting 26. Alternatively, a spring-action syringe or the like (not shown) can be utilized for creating a vacuum in chamber 16 for firmly holding the instrument on the cornea. The surgeon is thus enabled, with the aid of co-axial illumination, to establish the true optical center and to maintain fixation of the instrument on the eye so that incisions made into the cornea are rendered stable, centered, and reproducible.

As shown in FIGS. 3, 5, and 6, a plurality of pivot means 27 are provided on upper wall 13 of instrument 10 for pivotally mounting scalpel 11 about a fixed pivot axis for arcuate movement in each plane of incision. In the embodiment illustrated, each pivot means 27 comprises a pair of annular ribs 28, secured on upper wall 13 of the instrument and disposed in straddling relationship on either side of a respective slit 18. The upper ends of the ribs are arcuate to engage like-shaped arcuate pivots defined at the apexes of inverted V-shaped recesses 29 formed on a lower end and on either side of a handle 30 of scalpel 11, as shown in FIGS. 6 and 7. As further shown in FIG. 6, scalpel 11 is thus adapted to be pivoted between its full and phantom line positions to pivot blade 19 of the scalpel through an arc of incision. As shown, the blade preferably has a cutting edge formed on each side thereof so that the blade will cut in either direction as it is pivoted either toward or away from the center of the cornea. As further shown in FIG. 7, the longitudinal axis of handle 30 of the scalpel is offset relative to the longitudinal axis of blade 19 so that the handle does not obstruct the surgeon's view of the operation during pivoting of the blade.

It should be noted in FIG. 7 that the opposite outer sides of the lower end of handle 30 can be suitably configured to alternately engage indented surfaces 13a and 13b of the instrument which provide stop means limiting the arcuate movement of the blade and thus the length of the incision. In addition or alternatively, the converging surfaces, defining the legs of each V-shaped recess 29 and merging with the arcuate pivot at the apex thereof, can be suitably configured to engage converging surfaces 28a and 28b to also provide stop means for limiting the extent or length of the incision.

In carrying forth radial keratotomy on a patient, the surgeon would select an instrument 10 which has been predesigned and fabricated for the particular operation to be performed. A pair of diametrically positioned handles 31 may be formed integrally with outer wall 15 of the instrument to extend radially outwardly therefrom. The handles will aid the surgeon in holding the instrument, thus fixing the patient's eye which might otherwise tend to move. The optical zone comprising aperture 20, the length of each slit 18, and the orientation of the slits would be preestablished by a manufacturer to suit the needs of the surgeon. In addition, the height of ribs 28, the axial distance between the pivotal ends of the ribs and arcuate surfaces 21 which engage the cornea, and the effective length of scalpel blade 19 from pivot recesses 29, would be predetermined to precisely control the depth of incision, i.e., the distance the end of the blade projects past arcuate surfaces 21 for incision-making purposes.

As discussed below in reference to scalpel embodiments 11a and 11b (FIGS. 11-14), it may prove desirable to provide means for adjusting the blade relative to the handle of the scalpel to aid in providing such design parameters. The cutting excursion of the blade must not penetrate the inner surface of the cornea. The blade should cut deeply into the cornea, e.g., ninety percent (90%) of its depth, but not enter the cornea into the anterior chamber of the eye. The radial distance of ribs 28 from longitudinal axis A of the instrument (FIG. 5) and the diameter of aperture 20 would also be designed to match the extent of a patient's myopia and initial K readings, for example.

A circular stop 32 in ring-form is preferably secured internally of aperture 20 and at its lower end to provide additional stop means (along with surface 13a) to delimit the radially inner end of each slit 18. The additional stop means will function as a fail-safe device to prevent the blade from cutting further inward toward the center of the cornea, even should it slip as it is pivoted on the instrument. The ring-like stop means can be formed with the required predetermined radial thickness and could have one or more slits 33 of predetermined depth formed externally thereon (FIG. 6) and in radial alignment with a respective slit 18. This would allow variable control of the "optical zone" left intact at the conclusion of the operative procedure.

Once the instrument has been fixedly secured to the cornea, the surgeon holds the instrument by handles 31 and proceeds to sequentially insert blade 19 of scalpel 11 into slits 18 and into pivotal engagement with ribs 28 to effect the desired incisions on the cornea. Since slits 18 are radially and circumferentially oriented symmetrically, relative to central axis A of the instrument which is colinear with the optical center of the eye, the depths and lengths of the slits will be substantially identical and uniformly spaced to avoid any potential astigmatism problem which could occur if the respective incisions were formed slightly differently, such as those formed pursuant to a conventional feedhand method. During the pivotal engagement between ribs 28 and recesses 29 of the scalpel, blade 19 will be stabilized in the center of a respective slit 18 to ensure that the incision is precisely made. Twisting of the ultra-thin blade is prevented by such pivotal engagement, as well as by the width of the slit which closely matches and is only slightly larger than the thickness of the blade.

It should be understood that various modifications can be made to instrument 10 without departing from the spirit of this invention. For example, as shown on a modified instrument 10' in FIGS. 8 and 9, the structural elements of the pivot means comprising ribs 28 and recesses 29 could be reversed, i.e., a pair of pivot pins 29' could be secured to scalpel 11 in lieu of recesses 29 and a pair of arcuate recesses 28' could be formed, in lieu of ribs 28, on an upper wall 13' to straddle each slit 18'. This configuration of the opposite surfaces defining recesses 28' will also provide a positive stop means to limit the rocking movement of the surgical blade in its intended excursion, i.e., engagement of opposite sides of the lower end of the scalpel's handle with such surfaces will determine the length of the incision. Furthermore, although eight slits 18' are illustrated for a particular radial keratotomy operation, it should be understood that any desired number thereof could be utilized for a particular operative procedure. Likewise, more than one pivot means 27 could be associated in radially spaced relationship with each slit 18'.

Also, the slits could be oriented differently, such as would be the case for certain patients wherein it proves desirable to provide "cross-hatch" incisions transversely across prior incisions. For example, FIG. 10 illustrates a modified instrument 10" wherein radial slits 18" are intersected by circumferential slits 34 for correcting astigmatism. It might also prove desirable to form an instrument with radial slits closely spaced in one meridian of the cornea and spaced further apart in other meridians.

As further shown in FIG. 10, pivot means 27 could be eliminated and the outer surface of an upper wall 13" of the instrument formed in any desired configuration (flat, concave, convex, etc.). The instrument, employing above discussed suction means 12, could be thus attached to a body area of a patient, such as the eye, and the surgical blade dragged along the entire length of a particular slit. As shown in FIGS. 10 and 10a, guide means in the form of a pair of slots 35 formed in surface 13" on either side of a particular slit 18" are adapted to be engaged by pins 29' (FIG. 9) of scalpel 11' to guide the dragging and cutting excursion of the blade along the slit. The axial distance between the ends of the pins is slightly smaller than the distance between the circumferentially spaced outer surfaces of the slots to provide a close-fit therebetween to prevent twisting of the scalpel and blade during the cutting excursion.

As suggested above, it is normally desirable for the incision to evenly penetrate the cornea approximately ninety percent (90%) of its thickness for radial keratotomy. Since the cornea is normally thinner (e.g., 0.5 mm) at its center than at its periphery (e.g., 1.0 mm), the depth of the incision will thus vary during the blade's excursion. The configuration of the bottom surface portions of the slots that are in sliding bearing contact with pins 29' adjacent to the slit, largely dictate the depth and extent of incision. For example and as shown in FIG. 10A, such bottom surface portions can be suitably curved to conform to the shape of a particular patient's cornea which could be generally spherical or egg-shaped or comprise compound or variable curvatures.

For example and as shown in FIG. 10A, the depth of slit 18", defined by the axial distance between the bottom surface of slot 35 and the underlying curved surface of the instrument contacting the cornea, increases in a radial direction, inwardly towards the center of the instrument.

FIGS. 11–14 illustrate additional scalpel embodiments 11a and 11b, each having a blade adjustment feature, both usable with above-described instruments 10, 10', and 10" (with suitable pivot means 29 and 29' being employed on the scalpels, when needed). Scalpel 11a of FIGS. 11 and 12 comprises a pair of handle portions 36 and 37 pivotally connected together by a pin 38. A locking means 39, such as a standard releasable detent, is provided for releasably locking the handle portions together.

The lower end of handle portion 36 has a plurality of pins 40 secured thereon that engage at their ends within a plurality of like-shaped and aligned recesses 41, formed in the lower end of handle portion 37, when the handle portions are closed and locked together. An adjustable blade 42 has a plurality of like-shaped holes 43 formed therethrough, adapted to receive one or more pins 40 therein, whereby the distance the cutting edge of the blade extends past the handle and thus the cutting depth can be adjusted upon release of the handle portions. Although the cross-sections of pins 40, recesses 41, and holes 43 can assume any desired shape, non-circular shapes (e.g., triangular or rectangular) are preferable to aid in limiting undue movement of the blade relative to the handle.

Scalpel 11b of FIGS. 13 and 14 comprises a pair of separable handle portions 44 and 45 secured together by releasable fastening means, shown in the form of set screws 46. An adjustable blade 47 has a plurality of holes 48 formed therethrough, adapted to receive one or more pins 49 therein which further engage within aligned recesses 50. The interdigitating pins, holes, and recesses are constructed and arranged to function similar to the corresponding ones of the FIG. 11 scalpel embodiment. If so desired, after blade 47 has been adjusted, the scalpel assembly can be further unitized by use of a standard epoxy adhesive, a conventional heat sealing technique, or the like.

Although instrument 10 has particular application to ophthalmologic surgery, it should be understood that it is adapted for use in other surgical procedures wherein one or more incisions are required to be made on other body portions of a patient in a closely controlled and reproducible manner.

We claim:

1. A cup-shaped surgical instrument comprising
   an upper wall,
   inner and outer walls spaced radially from each other to define a generally annular suction chamber therebetween open only at a lower end thereof,
   a plurality of circumferentially-disposed struts secured to said inner wall and extending radially outwardly into said suction chamber,
   slit means for receiving and guiding a narrow surgical incision forming means, separate from said instrument, therethrough and for guiding cutting movement of said incision forming means in a plane of incision, said slit means comprising a plurality of separate slits each having a length substantially greater than its width and each formed axially through a respective one of said struts, and
   access means formed through said outer wall for drawing a vacuum in said suction chamber and around said struts for releasably securing said instrument on a body area by suction.

2. The surgical instrument of claim 1 wherein said instrument is composed of a transparent material.

3. The surgical instrument of claim 1 further comprising an aperture formed centrally through said instrument and wherein each of said slits extends radially outwardly from said aperture.

4. The surgical instrument of claim 3 further comprising stop means secured on said instrument and adjacent to said aperture to delimit a radially inner end of each said slit to control the length of said slit.

5. The surgical instrument of claim 4 wherein said slits are circumferentially disposed about said aperture and said stop means comprises an annular stop member extending radially from said aperture.

6. The surgical instrument of claim 1 further comprising at least one handle secured externally on said instrument.

7. The surgical instrument of claim 1 further comprising pivot means for pivotally mounting said incision forming-means about a fixed pivot axis for pivotal movement in said plane of incision.

8. The surgical instrument of claim 1 further comprising guide means adjacent to each said slit for guiding the dragging and cutting movement of said incision forming means along said slit means.

9. The surgical instrument of claim 1 wherein lower surfaces of said inner wall and said struts are arcuately shaped.

10. The surgical instrument of claim 9 wherein said outer wall is cylindrical and lower surfaces thereof extend axially beyond said inner wall and said struts.

11. The surgical instrument of claim 1 wherein said slit means further comprises at least one circumferentially extending slit.

12. A radial keratotomy surgical instrument comprising a cup-shaped template having an upper wall and inner and outer walls spaced radially from each other to define a generally annular suction chamber therebetween open only at a lower end thereof, a plurality of circumferentially-disposed struts secured to said inner wall and extending axially downwardly from said upper wall and radially outwardly into said suction chamber from said inner wall, slit means formed axially through each of said struts for receiving a surgical incision forming means, separate from said instrument, therethrough and for guiding movements of said incision forming means in a plane of incision, said slit means including a plurality of circumferentially spaced and radially extending individual slits each formed axially through a respective strut of said instrument and each slit having a depth that gradually increases radially inwardly towards a center of said instrument, and access means formed through said instrument for drawing a vacuum in said suction chamber.

13. The surgical instrument of claim 12 further comprising stop means for limiting both radial outward and radial inward movement of said incision forming means in each of said slits and the length of said incision.

14. The surgical instrument of claim 13 wherein said stop means comprises means positioned on the upper wall of said instrument, adjacent to said slit means.

15. The surgical instrument of claim 12 wherein said instrument is composed of a transparent material.

16. The surgical instrument of claim 12 further comprising an aperture formed centrally through said instrument and wherein said slits are each formed axially through the upper wall of said instrument and extend radially outwardly from a center of said instrument.

17. The surgical instrument of claim 16 further comprising stop means secured on said instrument to delimit a radially inner end of each said slit.

18. The surgical instrument of claim 17 wherein said stop means comprises an annular stop member.

19. The surgical instrument of claim 12 further comprising at least one handle secured externally on said instrument.

20. The surgical instrument of claim 12 further comprising pivot means for pivotally mounting said incision forming means and wherein said pivot means comprises a pair of upstanding ribs secured on said instrument and disposed in straddling relationship on either side of each said slit.

21. The surgical instrument of claim 12 further comprising pivot means for pivotally mounting said incision forming means and wherein said pivot means comprises a pair of recesses formed on said instrument and disposed in straddling relationship on either side of each said slit.

22. The surgical instrument of claim 12 wherein lower surfaces of said inner wall and said struts are arcuately shaped to conform to the curvature of a cornea.

23. The surgical instrument of claim 22 wherein said outer wall is cylindrical and lower surfaces thereof extend axially beyond said inner wall and said struts.

24. An opthalmologic surgical instrument disposed on a longitudinal axis thereof comprising a one-piece cup-shaped template having an upper wall and inner and outer walls spaced radially from each other to define a generally annular suction chamber therebetween open only at a lower end thereof, a plurality of circumferentially disposed struts secured to said inner wall and extending radially outwardly into said suction chamber, access means formed through said template for drawing a vacuum in said suction chamber, and a plurality of individual aperture means, each comprising a slit formed through said upper wall and axially through a respective one of said struts, for accommodating and guiding a surgical incision forming means, separate from said ophthalmologic surgical instrument, therein.

25. The ophthalmologic surgical instrument of claim 24 further comprising means for mounting a holder for said incision forming means on said upper wall.

26. The ophthalmologic surgical instrument of claim 25 wherein said means comprises a pair of ribs secured on said upper wall in straddling relationship on either side of said slit means.

27. The ophthalmologic surgical instrument of claim 25 wherein said means comprises a pair of recesses formed on said upper wall in straddling relationship on either side of said slit means.

28. The ophthalmologic surgical instrument of claim 24 wherein lower surfaces of said inner wall and said struts are arcuately shaped to conform to the curvature of a cornea.

29. The ophthalmologic surgical instrument of claim 28 wherein said outer wall is cylindrical and lower surfaces thereof extend axially beyond said inner wall and said struts.

30. The ophthalmologic surgical instrument of claim 24 further comprising an aperture formed centrally and axially through said instrument and stop means adjacent to said aperture to to delimit a radially inner end of each of said aperture means.

31. The ophthalmologic surgical instrument of claim 24 further comprising at least one handle secured externally on said outer wall.

* * * * *